United States Patent [19]
Lehmer et al.

[11] Patent Number: 4,739,410
[45] Date of Patent: Apr. 19, 1988

[54] SUPERIMPOSED ANALOG VIDEO IMAGE ON PLOTTED DIGITAL FIELD TESTER DISPLAY

[75] Inventors: Donald E. Lehmer, Berkeley; William E. Humphrey, Oakland, both of Calif.

[73] Assignee: Humphrey Instruments, Inc., San Leandro, Calif.

[21] Appl. No.: 942,668

[22] Filed: Dec. 17, 1986

Related U.S. Application Data

[62] Division of Ser. No. 779,920, Sep. 25, 1985, Pat. No. 4,675,736.

[51] Int. Cl.⁴ .............................................. H04N 7/18
[52] U.S. Cl. .................................... 358/219; 358/93; 358/183; 358/210; 358/903; 351/226
[58] Field of Search .............. 358/93, 107, 183, 210, 358/219, 903; 351/226, 225, 224

[56] References Cited

U.S. PATENT DOCUMENTS

| | | | |
|---|---|---|---|
| 4,393,394 | 7/1983 | McCoy | 358/183 |
| 4,561,738 | 12/1985 | Humphrey | 351/226 |
| 4,599,611 | 7/1986 | Bowker | 358/183 |
| 4,634,243 | 1/1987 | Massof | 351/224 |
| 4,647,822 | 3/1987 | Masuda | 358/219 |
| 4,675,736 | 6/1987 | Lehmer | 358/219 |
| 4,679,920 | 7/1987 | Takashi | 351/226 |

Primary Examiner—Howard W. Britton
Attorney, Agent, or Firm—Townsend and Townsend

[57] ABSTRACT

In an eye field tester, a vidicon camera observes the eye being tested and relays the resultant low light level image to the periphery of a digital display. The digital display contains both an image of the eye on the periphery and the plot of the visual field of the eye under test in the center. The vidicon observing the position of the eye has its horizontal and vertical sync pulses software generated to presettable counters. These counters generate corresponding delayed horizontal sync and vertical sync pulses for the vidicon. As a result of the delayed sync pulses, the central eye image of the vidicon is offset to the periphery of the digital screen (typically to the upper left-hand portion thereof). The offset image is gated into character spaces on the digital screen utilizing software generated character attribute.

4 Claims, 5 Drawing Sheets

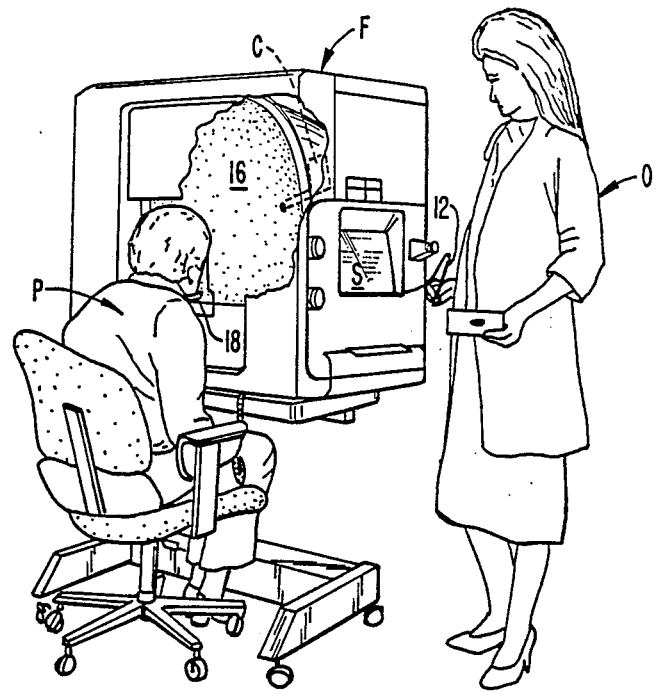
FIG.__1.
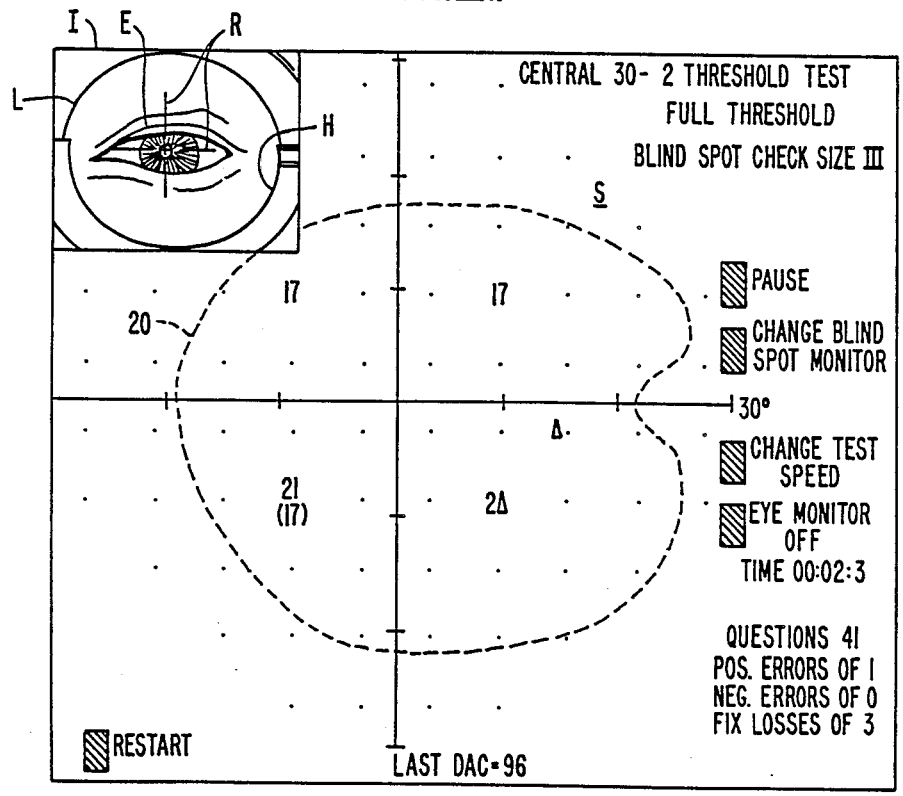
FIG.__2.

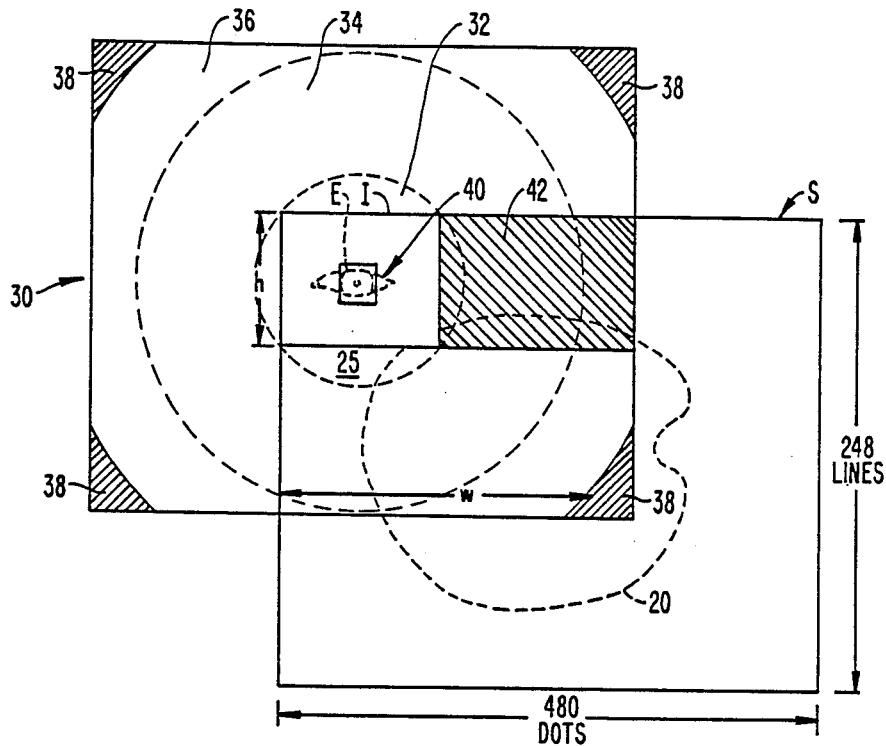
FIG._3.
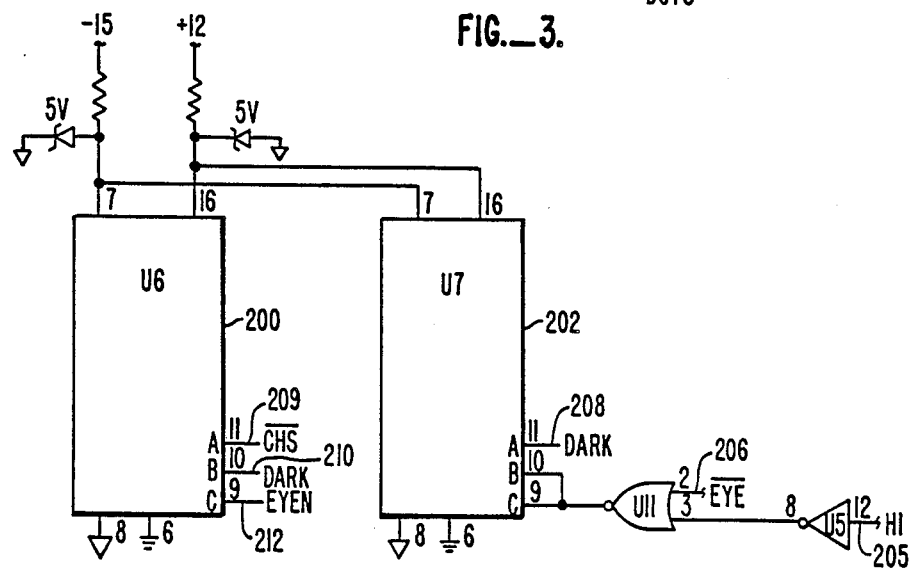
FIG._4C.

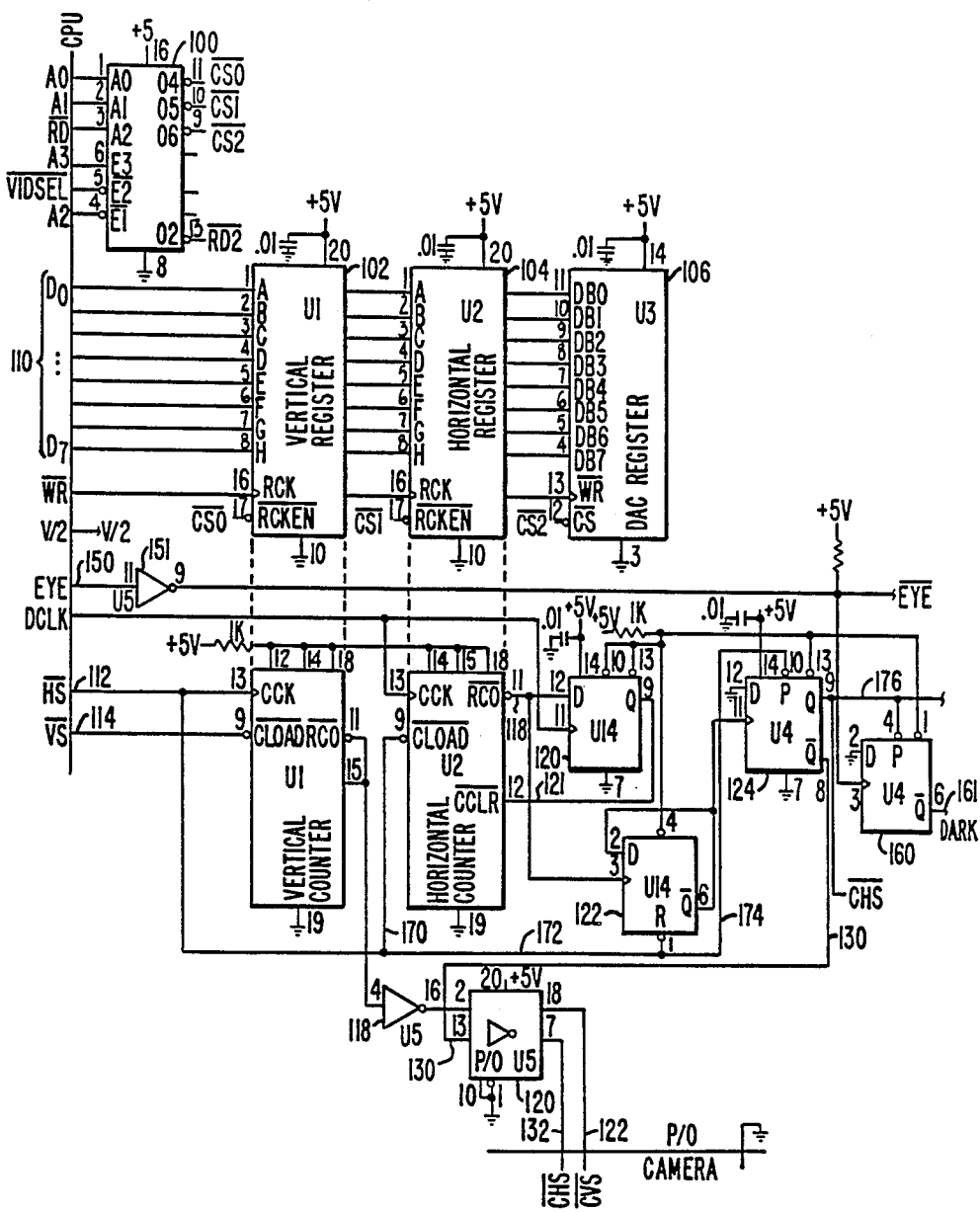
FIG._4A.

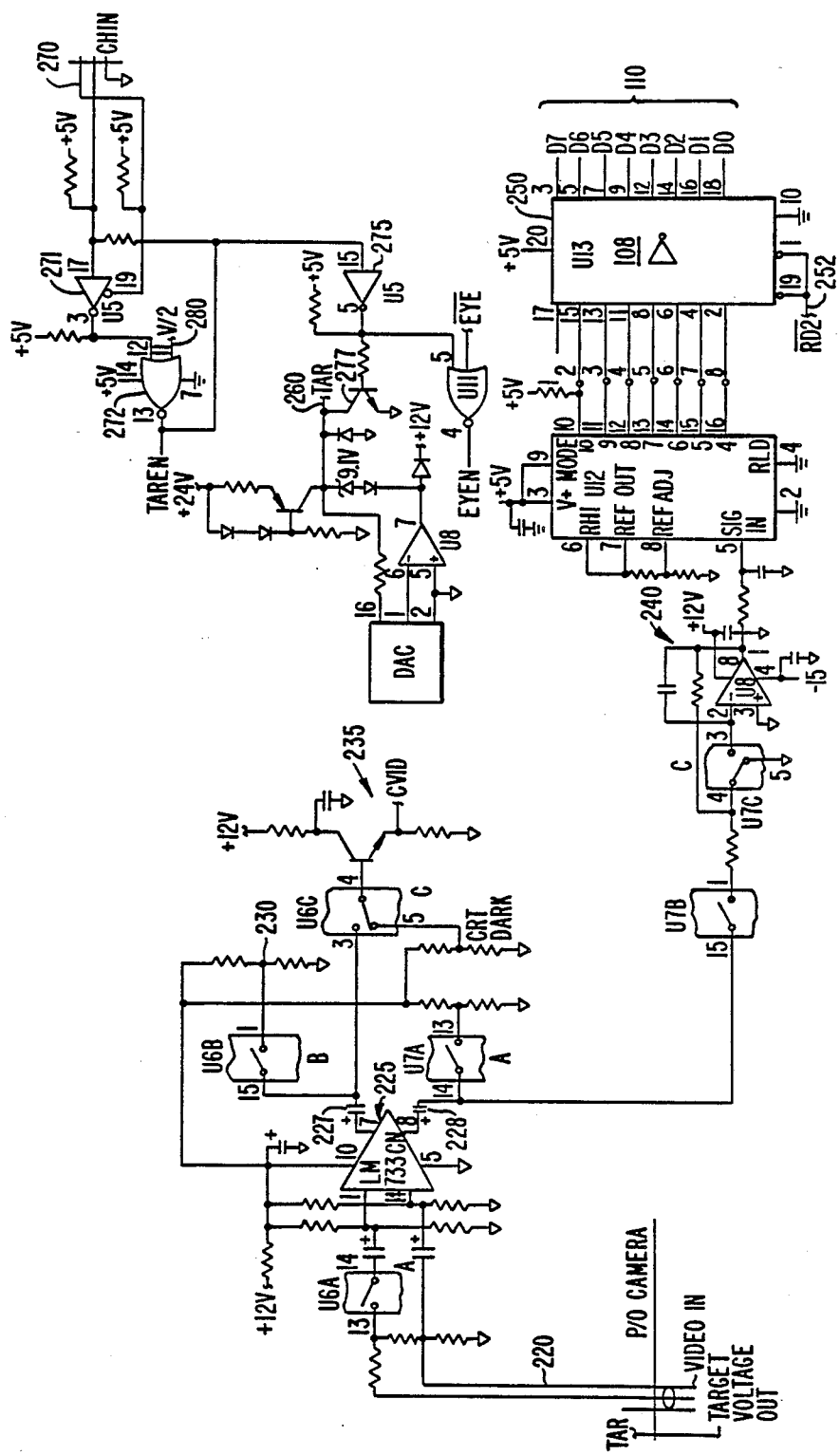
FIG._4B.

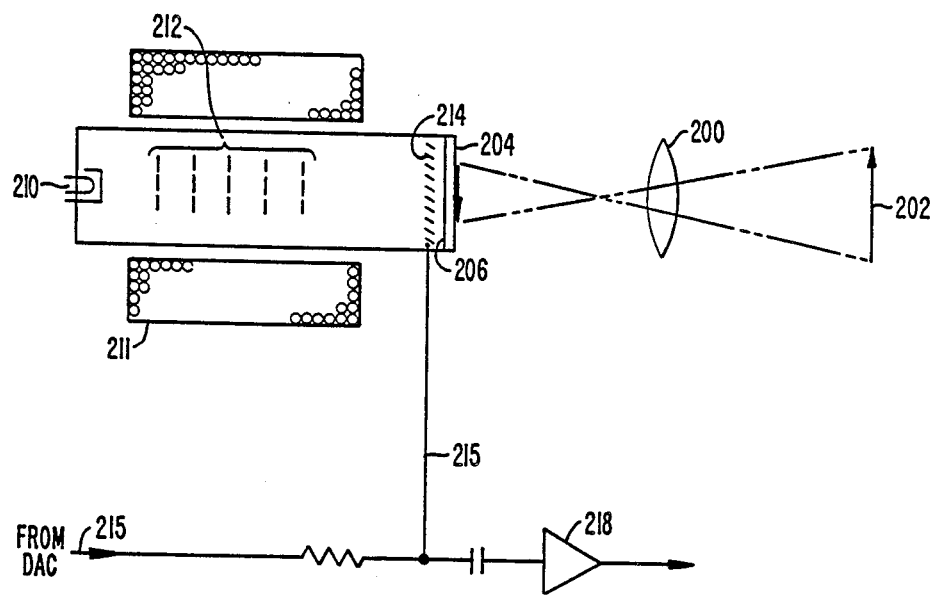
FIG._4D.

SUPERIMPOSED ANALOG VIDEO IMAGE ON PLOTTED DIGITAL FIELD TESTER DISPLAY

This is a division of application Ser. No. 6,779,920 filed Sept. 25, 1985, now U.S. Pat. No. 4,675,736.

BACKGROUND OF THE INVENTION

This invention relates to analog imaging on a digital screen and more particularly relates to the placement of the image of an eye on the digital map of the perimetry of the eye.

Description of The Relevant Art

Field testers for use in determining the perimetry of the eye are known. Typically, the patient is required to look straight ahead. Either a static image of light or a moving image of light is projected into the periphery of the patient's vision. Once the patient sees the image, the patient typically depress an indicator. Mapping of the location of patient notice occurs.

For analysis purposes, either the generation of a single map or the generation of a succession of maps at spaced time intervals plots the normal eye or the eye subject to disease. Medically beneficial information about the health of the observing retina is generated.

Computer generated plots for both displaying the location of the light when viewed by the individual are well known. Such instruments typically include a CRT digital display for viewing the map as well as a separate and adjacent means for determining whether the eye is centered.

Centering of the eye is understandably a problem. Assuming that a patient looks straight ahead and indicates truthfully the point of first sight on the periphery of the eye, a correct map can be drawn. However, when the patient pans his eye, typically to better view the image, errors occurs. This error occurs because as the retina of the eye is displaced so will the map of the eye likewise be displaced. It is important that the operator know that the patient is looking straight ahead.

Unfortunately, most instruments provide either a sighting device such as a telescope for observing the eye or alternately a separate CRT display for relaying a video picture of the eye. In either case, the operator's eye is distracted from the plot taking place. In trying to observe the image of the plot versus the image of the eye, operator confusion can and does occur.

SUMMARY OF THE INVENTION

In an eye field tester, a vidicon camera observes the eye being tested and relays the resultant low light level image to the periphery of a digital display.

In this document, the term "low light level sensitivity" will be used. This term refers to the fact that the vidicon is taking its image in a field of extremely low light. The vidicon has markedly degraded characteristics than when it operates under normal and much higher ambient lighting conditions. The camera operation protocol here disclosed enables use of a vidicon at these low light levels instead of the much more expensive substitution of an alternate camera such as a silicon target tube or charge coupled device.

The digital display contains both an image of the eye on the periphery and the plot of the visual field of the eye under test in the center. The vidicon observing the position of the eye has its horizontal and vertical sync pulses software generated to presettable counters. These counters generate corresponding delayed horizontal sync and vertical sync pulses for the vidicon. As a result of the delayed sync pulses, the central eye image of the vidicon is offset to the periphery of the digital screen (typically to the upper left-hand portion thereof). The offset image is gated into character spaces on the digital screen utilizing software generated character attribute. Use of the character attribute digitally maps the image to a precisely delineated portion of the digital display. Normally the analog image is superimposed over blank text characters.

As used in this application, the word attribute describes that commonly used character modifier that makes the same character appear with differing emphasis. For example, attribute can cause a character to appear in inverse video, underlined format, extra intensity, etc. In the normal character generator, there are eight discrete attributes available. As will hereinafter appear, we propose to use one attribute for the "playing" of the analog image to the screen and the "high brightness" attribute for the focus of the automatic gain control on the eye.

Use of the character attribute also permits the overlying plot of digital data on the analog image of the eye by writing non-blank characters in that area. For example, a digitally generated target reticle is placed over the analog image of the eye being tested.

Since the vidicon camera is subject to damage of its low light level sensitivity if subjected to bright images with high target voltage, the invention includes a system of controlling the camera image intensity using the target voltage only instead of adjusting amplifier gain. A view of the eye for purposes of gain control is software restricted by use of a different and additional character attribute to a digitally identified location at the expected area of the iris. The dark level of the low light image is set to be equal to the noise level adjacent the area of interest where light is obscured. A chin cup light detector is utilized to shut down camera operation when the patient viewing port of the instrument is not occupied to protect camera from bright images. There results a field tester having a display wherein the map of the eye and the panning and placement of the eye may all be observed simultaneously.

Objects and Advantages

An object of this invention is to disclose a method for centering an analog image such as that generated by a vidicon to an offset position on a digital display. According to this aspect of the invention, the vidicon camera is provided with delayed horizontal and vertical sync pulses. These pulses are generated by reading from software to presettable counters digital starting counts of varying values. Upon receiving the counts of varying values, the respective counters count out and generate ripple carryover. The ripple carryover latches circuitry to generate delayed vertical and horizontal sync pulses. Offset of the image of a vidicon can occur to virtually any portion of a plotted digital image.

Vidicons used at extremely low light level have only the central portions of their produced image usable. By restricting the observed data to the central portion of the vidicon image and displacing the total vidicon image, a vidicon generated low light level image of high quality results.

A further advantage of setting the presettable counters through software is that the displacement of the image relative to the digital image is adjustable. By changing the starting count of the vertical and horizontal sync counters, the image may be moved. Such movement may be used to align the image to the digitally generated target. Alternately, calibration of the image for initial camera alignment can occur.

Yet another aspect of this invention is that a small area of the vidicon camera is used for the analog image. As a result, the vidicon camera is fast even in a low light level environment.

A further object of this invention is to disclose an apparatus and method for the digital gating of the produced analog image to the screen display. According to this aspect of the invention, character attribute from character generation is used to digitally gate the image of the eye to a screen location. Typically, a digital map 22 characters long and 10 characters high is drawn in a 80 character by 31 character field. As a result, the analog image is digitally restricted to a precisely mapped location.

An advantage of this aspect of the invention is that the digitally painted aperture in combination with the displayed image moves the image of the eye anywhere on the screen that the operator may want it. Optimally, the analog image of the eye is placed on a periphery of the display where the operator can glance as an aside to make sure the eye is centered while watching the data plot.

A further advantage of using the attribute to digitally write the area for the analog image is that digital information may be plotted over the analog image. For example, a reticle is typically written and played over the center of the analog image (commonly delimited by a trial lens holder). Thereafter, the eye is placed and targeted on the reticle. Mapping of the perimetry can thereafter accurately occur.

A further object of this invention is to disclose an apparatus and method for adapting a vidicon camera to the extreme low light level within the field tester environment.

According to a first aspect of this invention, the conventional adjustable gain amplifier on a vidicon camera is set at maximum. Only the target voltage is used to increase and decrease image sensitivity. Low light level images are optimally observed without vidicon damage.

According to a second aspect of this invention, the gain control is gated in by a digital map to a finite character field area to observe the eye only at the pupil area and sclera surrounds. The gain control when optimally gated in by the digital map utilizes the iris area as the only pertinent background. The other portions viewed by the vidicon are ignored for gain control. The result is that the iris and pupil will be clearly visible.

An advantage of this aspect of the invention is that it has been discovered that the output of the gain control is sensitive to eye movement. Thus, where the patient pans his eye and thereby causes the validity of the test to be suspect, change in gain control output occurs as the sclera enters the area normally filled by the iris. This change can be used to flag undesired eye movement.

A third aspect of the adaption of the camera to low light level is to set the analog video level to known dark portions of the image. According to this aspect of the invention, character attribute is used to define a known dark portion of the image. This known dark level is gated to a floating circuit which circuit uses the "noise level" of the known dark area. As a result, the final analog video level is referenced to this dark level to compensate for any change.

A final aspect of the adaption of the vidicon camera to the low light level is to provide a chin cup light detector. The detector when not shut off from light as by the placement of a patient's chin, shuts down the target voltage or the vidicon. Consequently, the vidicon is not subject to image burn-in when the observing window of the disclosed is not occupied by the head of the patient.

Observing the improvement of this disclosure as a whole, the reader will realize that except for the addition of the vidicon camera, little need be done to the overall profile of a field tester. This minimum change of instrument profile readily suits this disclosure to retrofit instruments in the field or factory option.

BRIEF DESCRIPTION OF THE DRAWINGS

Other objects, features and advantages of this invention will become more apparent after referring to the following specification and attached drawings in which:

FIG. 1 is a perspective view illustrating a patient at a field tester with an operator at the screen of this invention;

FIG. 2 is a view of the field tester as seen by the operator showing the eye image displaced to the upper left-hand portion of the CRT display with the plotted perimetry image occupying the rest of the display;

FIG. 3 is a plot of the vidicon image overlaying the digital image with the two attribute maps on the digital image being illustrated so that the respective delays and digital mapping using attributes can be understood; and FIGS. 4A-4D are circuit maps of digital and analog circuitry illustrating the pertinent electronics of the utilized techniques.

DETAILED DESCRIPTION OF THE EMBODIMENTS

Referring to FIG. 1, a patient P is shown looking into a field tester F. Operator O observes a screen S containing the digital printout and analog image of this device. The operator operates a light pen 12 to activate through connected software the test.

The field tester F is shown partially broken away to expose a hemispheric bowl 16. Behind the hemispheric bowl 16 there is shown in phantom a vidicon camera C. The patient is shown with his head on a chin rest 18 with his eye braced into position looking straight ahead at an observation point. Typically, a lens holder and trial lens will be present. This is not shown in the view of FIG. 1. The video image of the holder H and lens L is shown in FIG. 2.

An optical system such as that disclosed in U.S. Pat. No. 4,561,738 entitled Field Tester issued Dec. 31, 1985, formerly patent application Ser. No. 436,878, filed Oct. 26, 1982 projects an image to the interior of the bowl. This image is typically scanned inwardly towards the patient's field of view at various intensities. When the patient first observes the image, he gives a signal, such as the depressing of a button (not shown). The point of image perception on the field of scan is plotted. Utilizing a plurality of points, the perimetry may be conventionally plotted as is well known in the art.

It will be understood that the vidicon camera V in effect "sees" the image of the eye through a small hole in the field tester globe. The side edges of the globe vignette most of the field of the vidicon. This being the case, the side edges of the image will in fact be dark. Thus, as will appear hereinafter more fully, the area 42 (see FIG. 3) will in fact be dark.

Referring to FIG. 2, the screen produced by this invention is illustrated. The screen includes a conventional perimetry plot 20 and an eye image area I shown up at the upper portion of the invention. Observing the eye image area I, several important observations may be made.

First, the eye of the patient E is viewed. It is centered in a digitally generated reticle R and is here shown looking straight ahead. A trial lens frame holder H contains a trial lens L. This is used where the patient is other than an emmetrope (as where the patient is a hyperope or a myope) to provide the patient with normal correction. With normal correction supplied, the results of the field test will accurately reflect the visual properties of the retina of the eye.

The advantage of the disclosed display will be apparent. The operator O must at all times observe the eye E on the reticle R centered and looking straight ahead. At the same time the progression of the automatically plotted data may likewise be observed. Discontinuities of data can be referenced immediately against eye position.

Turning to FIG. 3, the perimetry plot 20 at screen S is illustrated with the vidicon output 30 being illustrated.

In order to set forth this invention, the characteristics of the low light level image of the vidicon will first be set forth. Thereafter, displacement of the vidicon image 30 relative to the screen digital image S will be discussed. The placement of the image eye of the eye E in the upper left-hand corner of the screen S by displacement and image attribute will be discussed. Finally, the areas of gain control focus and noise level reference will thereafter be set forth.

The reader will understand that the environment of the low light level image is essentially hostile to the normal operation of the vidicon. To complicate this matter further, it has been proposed by others to take such perimetric examinations at two light levels—one light level being in effect ten times as bright as the "normal" and low light level. The disclosed design of this invention is made to accommodate these differing light levels.

For example, where the eye is viewed by the vidicon at a relatively high light level, and thereafter viewed by the vidicon at a low light level, a latent image present on the vidicon will destroy instrument usefulness. This loss of the instrument's usefulness would continue until the vidicon regained its normal sensitivity. The disclosed circuit has been developed to do away with this debilitating latent image problem.

Regarding the vidicon image 30, the particular vidicon used is a Separate Mesh Vidicon No. 8844 having a two-thirds of an inch aperture, a product of RCA company of Lancaster, Pa. This product may also be identified as a No. 20PE13A Panasonic vidicon camera vended by the Panasonic Corporation of Tokyo, Japan.

At low light levels, the vidicon has concentric rings of low light level sensitivity. A first and inner ring 32 provides an area of optimal low light level sensitivity. Surrounding area 32 is a concentric area 34 which area has reduced low light level sensitivity. Exterior of ring 34 is an area 36 which again at low light levels has relatively good sensitivity approaching that of the central area 32. Finally, and at the far periphery are areas of lost sensitivity 38. These respective areas 38 when viewed conventionally would be white areas on a discrete black and white camera monitor.

Viewing the areas of vidicon sensitivity, the reader will immediately understand that a peripheral use of the vidicon at the low light levels of the field tester will not work. Image artifact from the vidicon tube would rapidly obscure the intended image, if that image is taken on the periphery of the vidicon. This would be especially true of the vidicon in and around areas 38.

Having set forth the characteristics of the vidicon, image displacement can now be discussed.

In the below described electrical circuitry, the vidicon tube will be supplied with delayed horizontal and vertical scan signals.

Referring to FIG. 3 and remembering that the digital image S typically includes 248 horizontal scans and 450 character dots in a single horizontal scan, the delays can be quantitated. Character dots are those positional interval conventionally used for character generation on a digital display.

Regarding the vertical scan, it will be seen that a vertical scan should start approximately a little over half way through the preceding vertical scan of the screen S. Thus, the vertical sync pulse will be in the order of 135 line scans of the screen S. That is to say when the line scans reach the midportion of screen S, the vertical scans on the vidicon tube will begin. Thus, when the top horizontal scan line of screen S crosses the eye image area I, the vidicon scan will be at its central location.

The horizontal image scan may be similarly understood. When the horizontal scan of the screen S is approximately two-thirds complete, the beginning horizontal scan of the vidicon will be initiated. Thus, when the scan S returns to the eye image area I, the vidicon will be scanning the same coincident area.

It will be noted that we have described the initiation of vidicon scans in terms of delay. This is done because negative time does not exist. Thus, even though it appears that one would have the vidicon scan leading the screen scan, it lags the screen scan in all cases.

We have shown here the use of counters in a specific protocol to cause delay of the vidicon image relative to the digital image. The reader will understand that this is preferred. For example by changing the respective horizontal and vertical counts, it is possible to minutely adjust the image relative to the picture of the vidicon camera. For example, we can center the image of the reticle with respect to the lens holder. Further, the camera angle can be digitally corrected making installation easier and enabling adjustment of the image from time to time for calibration.

We contemplate other means for the respective delay of the horizontal and vertical scan of the vidicon image. For example, a one shot multivibrator circuit could as well be used. Likewise, delay schemes using various timers—hardware and software—can be substituted for the preferred embodiment of the counter scheme disclosed herein.

It will be understood that the automatic gain control to the vidicon camera must be restricted. Restriction is required to set the gain control to the iris area of the eye. Accordingly, an attribute (for example, high intensity) is software programmed to register with area 40. This signal selects the analog data for gain control.

Having set forth the schematics with respect to FIG. 3 of the overlay of the vidicon image on the digital display, attention can now be directed to the pertinent circuitry.

Regarding the pertinent circuitry, the digital circuitry will first be explained with respect to FIG. 4A. The analog circuitry will be explained with respect to FIGS. 4B and 4C. The camera will be schematically referred to in FIG. 4D.

Referring to FIG. 4A, a decoder 100 including address inputs A0-A2 and respective read and video select inputs, (RD and VIDSEL), outputs addresses CS0-CS2, RD2. These respective addresses enable a vertical counter 102 (CS0), a horizontal counter 104 (CS1), and a digital to analog converter 106 (CS2) and an analog to digital converter (RD2) 108 (see FIG. 4B). Presettable counters 102, 104, DAC (digital to analog) register 106, and ADC (analog to digital) register 108 are connected to bus 110 and conventionally software addressed. The values received are latched and thereafter conventionally read to the counter portions.

Horizontal sync is generated by a conventional computer circuitry for the digital display. This is not shown. The horizontal sync appears at output 112 from the digital display. The vertical sync is similarly generated and appears at output 114. The function of producing a delayed vertical sync will be discussed with respect to counter 102. Thereafter the function of obtaining horizontal sync will be discussed with respect to counter 104.

With respect to the vertical sync pulse, this signal is output at line 114 to counter 102. The counter on receiving this pulse is loaded with the number latched at register portion of counter 102.

Line 112 provides the line count and decrements the vertical sync counter 102. The counter once loaded increments until full and outputs at ripple carryover 116. The ripple carryover 116 is inverted at inverter 118 and is output on the camera vertical sync at 122. The output at 122 commences the camera vertical scan on a delayed basis dependent upon the software count loaded into counter 102. Offset of the vidicon image thus vertically occurs.

Horizontal sync is analogous but is more complex. Because the desired analog image location is over 256 character dot locations along the horizontal scan, it is required to cycle the 256 counter twice for displacement of the image to the upper left-hand corner of the digital display. As will be seen, counter 104 also actuates additional circuitry to allow sampling of the dark area.

Referring to counter 104 and remembering that each horizontal scan is approximately 480 dot clocks long, it will be seen that the beginning of the vidicon scan must start at two-thirds of a horizontal scan. Broadly, counter 104 is a 256 counter. This counter is first loaded with a count allowed to ripple carryover, reset to a zero count and fully count. Once the counter is fully counted out, the ripple carryover commences the horizontal sync at a point where the horizontal scan of the digital display S is approximately two-thirds of its cycle.

Typically, counter 104 is preloaded with a number in the order of 190. The counter counts out in 65 counts with clock counts being received from DCCK on line 116. A ripple carry out at line 118 is passed through a D flip-flop 120. The Q of D flip-flop 120 output on line 121 resets counter 104 to zero for a full countout.

The countouts of counter 104 on line 118 is received at a divide by two flip-flop 122. This flip-flop, having the D and $\overline{Q}$ bar output outputs to a third D flip-flop 124. Flip-flop 124 latches the second overflow of the counter and outputs on its $\overline{Q}$ bar output on line 130 the generated horizontal sync pulse for the camera. The horizontal sync pulse 130 passes through a buffer to the horizontal sync output 132.

The reader will remember that it is also necessary to activate a view of the dark level. See area 42 on FIG. 3. To accomplish this result, the computer generated eye attribute is received in at line 150, inverted at line 151 and utilized to set a fourth flip-flop 160 at the end of the eye area. Fourth flip-flop 160 outputs reading of the dark signal at 161 and is reset at camera horizontal sync. Area 42 is thereby established for image dark level (See FIG. 3).

When the horizontal sync pulse is received, reset of the circuitry occurs. Specifically counter 104 is preset to predetermined count by line 170. D flip-flop 122 is reset at line 172, D flip-flop 124 reset at line 174, and D flip-flop 160 reset by the Q output at line 176. The described cycle repeats for the next line scan.

Having set forth the delay circuitry, attention will now be directed to circuitry for gating the analog image of the eye to the digital display.

Referring to FIG. 4C, CMOS switch drivers 200 and 202 can be seen. These switch drivers drive switches U6A, U6B, U6C, U7A, U7B, and U7C.

The switch drivers 200 and 202 are driven by timing signals generated by the counters 102 and 104. U6A is driven by $\overline{CHS}$ which is the complement of the camera horizontal sync, previously set forth. U6B is driven by the dark signal from line (DARK) 160. U6C is driven by EYE, the attribute that turns on the camera.

U7A is driven by DARK. U7B and U7C are driven by AND logic of the automatic gain control attribute (HI) at 205 and the EYE attribute at 206.

Having seen the driving arrangement of FIG. 4B, the placement of the driven switches from FIG. 4C can now be set forth. The gating of analog camera signals as well as camera control can be understood.

Video from the camera is into the circuit on lines 220. Camera generated horizontal sync is removed at switch U6A by $\overline{CHS}$ opening the switch. The signal passed through an amplification circuit generally denominated 225, the removed camera horizontal sync preventing amplified artifact in the output image of the camera.

Observing the circuit as it comes out of the amplifier, paired capacitors 227 and 228 cause the camera output to float. The upper portion of the circuit includes a voltage divider 230. Switch U6B is closed during the sweep of the vidicon at area 42. Thus the "dark" level of the analog signal is set to a voltage reference by area 42 of FIG. 3.

When the eye is to be output to the digital display, switch U6B opens and U6C closes to output 4 to permit the video signal to output through switch U6C and amplifier 235 to the digital video display. The analog video data is mixed with the digital video which may occur at the same time.

It will be understood that the operation of switches U6B and U6C to the analog image portion of the digital display are in the alternative. Therefore, once the level of the circuit has been set to dark voltage, amplification will be above the particular dark voltage set.

Switch U6C toggles to set the lower leg of the output of amplifier 225 to a complimentary dark voltage when the video display is dark. Through switch U7A, this signal is switched during the dark time of the image on the vidicon to set the corresponding dark level to the ambient noise.

When the digital signal is within the eye area I, the automatic gain control attribute is ANDed to form area 40. This connects the automatic gain control to the video signal through switch U7B. Switch U7C switches the video level to the automatic gain control voltage sample and hold amplifier 240. The function of sample and hold amplifier 240 is to hold the analog level of the video signal in area 40 to produce a continuous input to the analog to digital converter 245. Converter 245 permits observing the average light intensity of the area 40 immediate the eye. As will be apparent, the size of this target area may be software tailored.

Analog to digital converter outputs to a register 250. Register 250 is read when a read enable line 252 enables such reading to the computer bus 110. The resultant signal is conventionally digitally processed.

Control of the level of the camera video signal is done via the vidicon target voltage generated at digital to analog converter 106 (FIG. 4A) being input on line 260. This voltage is passed through applicable circuitry and output to the target voltage of the vidicon. The greater the target voltage, the higher the level of output. It will be noted that the conventional adjustable gain has been set to maximum.

It is necessary to either drastically lower the target voltage or to shunt the target voltage control to ground to turn off camera where high light conditions are observed. This is done by the chin up detection. Alternatively it is desirable to turn the camera off when the computer is not operating.

Regarding shunting the voltage to ground when a chin is not located in the chin detector, a chin detector at 270 seeing light and thereby outputting a signal causes an amplified signal to be passed out of an amplifier 271 through a NOR gate 272. The output passes through an amplified inverter 275 to a transistor 277. Transistor 277 is thus turned on when the chin detector at 270 sees light. No target voltage will appear. The vidicon camera will be shut down in high ambient brightness when the chin detector is not eclipsed and will thus not "freeze in" high intensity light images.

Additionally, and when the computer is inactive, a signal V/2 is generated. A signal appears on line 280 from the computer to the nor gate 272. Again, the current to the camera target voltage is switched to the OFF position.

It has been found that the disclosed automatic gain control circuitry is highly sensitive to the displacement of the eye. For example, the perimetry test takes a time period in the order of one half hour. Where the eye is panned, the automatic gain control circuitry is highly sensitive to movement of the eye. Typically the circuit indicates a much brighter image as more sclera comes into view or an eyelid is presented to the vidicon.

Therefore, the reader will understand that fluctuations in the level of the output of the gain control can be used for indication of undesired eye movement. For example, the software can be programmed to indicate large eye movements by shifting the boarder of the analog display on FIG. 3 to inverse video.

The vidicon camera only need be briefly described. A lens 200 images an object 202 at camera image 204 on photosensitive screen 206. An electron beam generated at source 210 is deflected by electrical yoke 211. This beam passes through grids 212 to screen 206. Target voltage 215 passes to vidicon target 214 and varies the intensity of the output. Amplifier 218 generates the analog video output and is locked in maximum gain.

What is claimed is:

1. In combination:
   a field tester for generating a perimetric map of the human eye;
   a video camera for observing the eye of a patient being tested in said field tester and generating an analog video image of said eye;
   a computer operably connected to said field tester for generating a perimetric map of the patient's eye;
   a digital image display with said computer having a dot clock, a horizontal sync signal and a vertical sync signal;
   said digital image display operably connected to said computer to display said perimetric map of said field tester and said analog video image of said eye;
   a character generator for said computer for writing over said digital image characters in discrete character spaces, said characters having attribute for changing character style while permitting characters to be generated;
   means connected to the software of said computer for writing character attribute to the location of the analog image of said eye on said digital image;
   means outputting from said digital image at said written character attribute to said video camera a gain control signal from said written attribute spaces only whereby the gain control on said video camera in said field tester is controlled by said attribute written intervals on said image only.

2. The invention of claim 1 and wherein changes in said gain control signal are output to indicate movement of said patient's eye.

3. In combination:
   a field tester;
   a computer connected to said field tester for generating a digital image of the perimetry of a patient's eye;
   a patient observing station having a detector for indicating the presence of a patient;
   a digital display connected to said computer having a dot clock, a horizontal sync output and a vertical sync output;
   a video camera for generating an analog image of said patient's eye, said video camera having light sensitivity, said video camera having a means for controlling said camera gain;
   means for shunting said gain control to a lower potential upon a patient being absent from said patient observing station; said means including a light sensitive detector.

4. The invention of claim 3 and further including means for shunting said gain control to ground upon said non-operation.

* * * * *